(12) United States Patent
Bargh et al.

(10) Patent No.: US 10,876,963 B2
(45) Date of Patent: Dec. 29, 2020

(54) DEVICES AND METHODS FOR IMPROVING AND EVALUATING STABILITY OF PUMPED PROTEIN SOLUTIONS IN BIOPROCESSING SYSTEMS

(71) Applicant: The Automation Partnership (Cambridge) Limited, Royston (GB)

(72) Inventors: Adrian Neil Bargh, Royston (GB); John Paul James Betts, London (GB)

(73) Assignee: The Automation Partnership (Cambridge) Limited

( * ) Notice: Subject to any disclaimer, the term of this patent is extended or adjusted under 35 U.S.C. 154(b) by 0 days.

(21) Appl. No.: 16/641,224

(22) PCT Filed: Oct. 5, 2018

(86) PCT No.: PCT/EP2018/077111
§ 371 (c)(1),
(2) Date: Feb. 21, 2020

(87) PCT Pub. No.: WO2019/068855
PCT Pub. Date: Apr. 11, 2019

(65) Prior Publication Data
US 2020/0225156 A1    Jul. 16, 2020

(30) Foreign Application Priority Data
Oct. 6, 2017   (EP) .................................. 17001651

(51) Int. Cl.
*G01N 21/00*   (2006.01)
*G01N 21/53*   (2006.01)
(Continued)

(52) U.S. Cl.
CPC ......... *G01N 21/53* (2013.01); *F04B 43/1284* (2013.01); *G01N 33/6803* (2013.01)

(58) Field of Classification Search
CPC .............. G01N 21/53; G01N 15/0205; G01N 15/1459; G01N 21/51; G01N 15/1434
(Continued)

(56) References Cited

U.S. PATENT DOCUMENTS 4,973,675 A    11/1990  Israel et al.
5,230,614 A     7/1993  Zanger et al.
(Continued)

FOREIGN PATENT DOCUMENTS

AU    2015 202 699 B2    6/2015
DE   10 2010 014607 A1   10/2011
(Continued)

OTHER PUBLICATIONS

International Search Report and Written Opinion, dated Jan. 14, 2019, for International Patent Application No. PCT/EP2018/077111, 13 pages.

*Primary Examiner* — Md M Rahman
(74) *Attorney, Agent, or Firm* — Klarquist Sparkman, LLP

(57) ABSTRACT

The present invention relates to devices and methods for improving and evaluating stability of pumped protein solutions in cross-flow filtration applications. Inter alia, the present invention provides a peristaltic pump for cross-flow filtration having a pump head, wherein the pump head comprises a stepped occlusion plate and at least one pump roller, wherein a tubing is to be arranged between the stepped occlusion plate and the at least one pump roller, wherein the stepped occlusion plate has a specific configuration.

9 Claims, 1 Drawing Sheet

(51) Int. Cl.
*F04B 43/12* (2006.01)
*G01N 33/68* (2006.01)

(58) Field of Classification Search
USPC .......................................................... 356/338
See application file for complete search history.

(56) References Cited

U.S. PATENT DOCUMENTS

| | | |
|---|---|---|
| 6,051,268 A | 4/2000 | Mahmoud et al. |
| 6,149,621 A | 11/2000 | Makihara |
| 2008/0277343 A1* | 11/2008 | Schick .................. B01D 15/14 210/650 |
| 2012/0148415 A1 | 6/2012 | Brueckner |
| 2015/0056710 A1 | 2/2015 | Reed et al. |
| 2017/0191022 A1 | 7/2017 | Lipkens et al. |

FOREIGN PATENT DOCUMENTS

| | | |
|---|---|---|
| EP | 1 623 752 A2 | 2/2006 |
| FR | 2 503 799 A1 | 10/1982 |
| FR | 2 871 857 A1 | 12/2005 |
| WO | WO 98/50699 A1 | 11/1998 |
| WO | WO 02/25112 A1 | 3/2002 |
| WO | WO 2011/133997 A1 | 11/2011 |
| WO | WO 2012/135834 A2 | 10/2012 |

\* cited by examiner

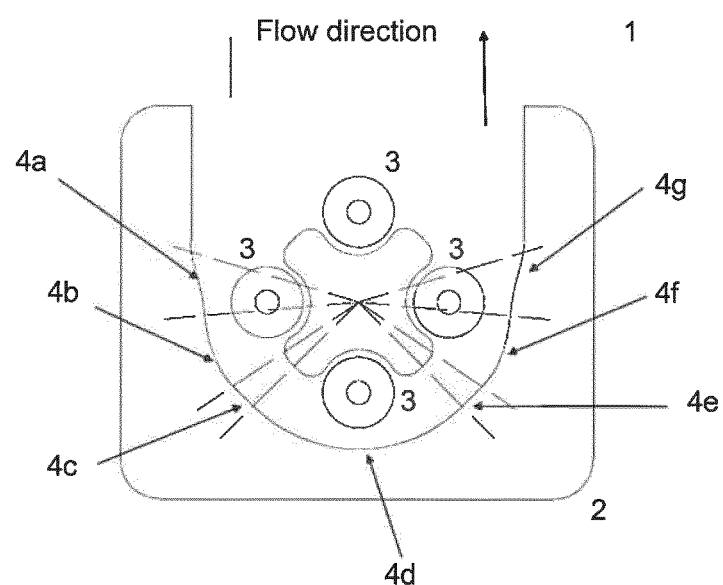

DEVICES AND METHODS FOR IMPROVING AND EVALUATING STABILITY OF PUMPED PROTEIN SOLUTIONS IN BIOPROCESSING SYSTEMS

CROSS REFERENCE TO RELATED APPLICATIONS

This is the U.S. National Stage of International Application No. PCT/EP2018/077111 filed Oct. 5, 2018, which in turn claims the benefit of European Patent Application No. 17 001 651.3, filed Oct. 6, 2017. European Patent Application No. 17 001 651.3 is incorporated herein in its entirety.

The present invention generally relates to devices and methods for improving and evaluating stability of pumped protein solutions in bioprocessing systems.

In methods of processing proteins used in biotechnology or similar technical fields, some proteins are easily damaged during processing, like, for example, in cross-flow filtration. Said proteins are referred to being shear sensitive. However, "shear" is often a misused term as damage from various causes are often just labelled as shear damage when the real cause is often unknown. Thus, in the present specification, the term protein damage is used to encompass all the effects.

In small-scale (laboratory) protein processing systems, there are many aspects that are worse when compared to larger scale (industrial) protein processing systems. One example is that in small-scale systems the surface area to volume ratio is increased and therefore the consequence of any surface related protein damage is more significant.

Such damage to the protein, typically impacts on the tertiary and secondary structure of the protein, may manifest itself in a number of ways, for example, formation of insoluble aggregates resulting in "cloudiness" in protein solutions.

Thus, in general it is difficult to pump protein solutions, for example in cross-flow filtration or ultrafiltration/diafiltration (UF/DF) systems, while protein damage is minimized, and to reduce the level of protein damage in a small-scale system to a level similar to that observed in a larger scale system.

The latter of the above two aspects is particularly important, as small-scale devices are critical to rapid process development, particularly when the availability of valuable proteins is limited, as in early development of biological therapeutic molecules.

It is important that the small-scale model can demonstrate the sensitivity of the protein under test to physical abuse in the system. As such the small-scale system must effect the same level of physical abuse on the protein as a larger scale system such that the relative robustness of different protein candidates can be assessed and differentiated with respect to the predicted performance in the large-scale system. Therefore, the additional protein damaging effects resulting from the smaller scale of the system must be compensated in some fashion.

Findings in experiments carried out by the present inventors indicate that some combination of the features of tubing materials, like, for example, surface properties and construction material composition, play a major role in the amount of protein damage. As defined here, protein aggregation is a form of protein damage. Proteins can be damaged during various unit operations in bioprocessing as described above, like, for example, filtration processes. In the experiments leading to the present invention it has been investigated how different pumps and tubing impacted on protein damage, in particular the formation of insoluble protein aggregates.

A number of hypotheses can be formed for the basis of such effects. These include, but are not limited to:

i) a tube material that does not "bind" or interact with the protein may be preferable to a tubing where there is interaction and interference with the integral molecular forces retaining the three-dimensional structure of the protein, ii) tubing surface smoothness is also thought likely to play a role. A rough surface may trap small pockets of liquid when the tubing surfaces are compressed together, iii) tubing that does not spread when compressed reduces mechanical stress on any protein caught between the tubing surfaces as a peristaltic pump roller passes.

It has been found that certain tubing types, like, for example, tubing made of Marprene™, Bioprene™ and Santoprene™, cause significantly more protein damage compared to a silicone tubing. The current state of the art is that Marprene™, Bioprene™ and Santoprene™ tubing and similar tubing are often the preferred choice for peristaltic pumps, as these types of tubing have a long life with low spallation.

Although silicone tubing has been found to create less protein damage than Marprene™ tubing, etc., the amount of damage is still significant. The reason may be that a typical silicone tubing used in a peristaltic pump is relatively elastic. The tubing deforms significantly by the force of the rollers of a peristaltic pump. The tubing internal tube surfaces may stretch 30% as the pump rollers pass and this stretching is thought to contribute to protein damage. For small-scale applications a typical tubing internal diameter is 1.6 mm (1/16") with a wall thickness of 1.6 mm (1/16"). Typically, the two walls of the tubing would be compressed to a dimension of less than 2.0 mm by the pump roller.

One way to reduce the amount of tubing deformation would be to use a stiffer tubing. However, this requires a higher force to compress the tubing with a resulting higher motor torque requirement and shorter tube life.

A preferred method of reducing tubing deformation is to mechanically reinforce the tubing to reduce longitudinal and transverse tubing deformation. Mechanical tubing reinforcement is typically done using braided nylon in the wall of the tubing. This mechanical reinforcement is typically done to increase the pressure capability of the tubing.

Further findings in experiments carried out by the present inventors indicate that the amount of pulsation from a peristaltic pump and the amount of roller load applied to the tubing by the peristaltic pump causing mechanical damage to the tubing and the proteins also play a major role in the amount of protein damage.

There are two main factors that control the amount of pulsation from a peristaltic pump. The most obvious is the rate of the roller decompressing the tubing and is largely independent of pressure. The profile of the occlusion plate can be designed to reduce the amplitude of pulsation caused by decompressing the tubing. The other cause of pulsation is the elasticity of the tubing and is dependent on pressure. The explanation of the latter point is as follows. The pressure in a section tubing pinched between two rollers of a peristaltic pump is approximately equal to the inlet pressure of the pump and is typically at atmospheric pressure, whereas, the downstream pressure is typically higher than atmospheric pressure, for example, up to 4 bar for cross-flow filtration. When the section of tubing between the rollers is exposed to the higher downstream pressure there is a very sudden reverse flow of liquid that pressurises the lower pressure section. The reduced amount of high speed reverse flow of liquid may also be a factor in reducing protein shear damage.

Moreover, the roller load applied to the tubing by the pump should be minimized in order to minimize mechanical damage to the tubing and the proteins.

Finally, to minimise protein damage the tubing in the pump should be compressed by the rollers for the minimum possible distance. However, pumps designed to minimise pulsation, typically have a gradual "lead in" and "lead out" of the pump occlusion plate such that the tubing is compressed and decompressed gradually. The gradual "lead in" and "lead out" may double the length of compressed tubing and therefore increases the rate of protein damage. Therefore, there is a conflict between the requirements of low protein damage and low pulsation.

In view of the above, an object underlying the present invention is to provide devices and methods for improving and evaluating stability of pumped protein solutions in cross-flow filtration applications.

This object is solved according to the invention by the features of the independent claims. Advantageous and expedient embodiments of the invention are apparent from the dependent claims.

According to an aspect of the present invention there is provided a peristaltic pump with a pump head for cross-flow. The pump head comprises a stepped occlusion plate and at least one pump roller. A length of tubing is to be arranged between the stepped occlusion plate and the at least one pump roller. The stepped occlusion plate has an initial tubing compression lead in section, a constant compression lead in section, a lead in-to-pumping step, a constant full tube compression pumping section, a pumping-to-lead out step, a constant compression lead out section, and a final tubing decompression lead out section.

The initial tubing compression lead in section is adapted to provide an initial rapid tubing compression. The constant compression lead in section and the constant compression lead out section are adapted to bring the internal tubing surfaces close to each other. Specifically the internal tubing surfaces are not touching. In other words, the internal tubing surfaces are contact free. The lead in-to-pumping step and the pumping-to-lead out step are adapted to fully pinch the tubing closed by the at least one roller. The final tubing decompression lead out section is adapted to provide a rapid full decompression of the tubing.

Thus, the pump head design of this invention uses a stepped occlusion plate. At the start of the occlusion plate lead in section, there is an initial rapid tubing compression and then a constant compression lead in section, where the internal tubing surfaces are close to each other, but not touching. The transition from the lead in to the pumping section is a small step to fully pinch the tubing closed by the rollers. At the end of the pumping section there is a small step to the lead out section, where the tubing is not fully pinched (similar to the lead in section). At the end of the lead out section there is a rapid full decompression of the tubing. Therefore, due to the pump head design of this invention, the tubing in the pump head is compressed for the minimum possible distance compared to prior art pump head designs.

According to a further embodiment of the present invention, the pump head has 1, 2, 3 or 4 or even more rollers. The number of rollers will be selected by the skilled person depending on the requirements of the system.

According to a further embodiment of the present invention, the peristaltic pump is a sprung occlusion plate peristaltic pump, wherein the pressure of the sprung occlusion plate on the tubing can be adjusted.

According to a further embodiment of the present invention, the peristaltic pump is a sprung roller peristaltic pump, wherein the pressure of the at least one roller on the tubing can be adjusted.

According to said embodiments including a sprung occlusion plate or at least one sprung roller, the roller load applied to the tubing by the pump and hence mechanical damage to the tubing and the proteins can be minimized.

Specifically, this may be done by first defining the maximum pressure that the pump needs to generate for a particular process and then designing and/or configuring the pump to just meet that pressure requirement with a minimum safety margin. The pressure capability of a peristaltic pump depends, amongst other things, on the amount of force applied to the tubing by the roller. The roller force adjustment can be done either manually or automatically. In a sprung roller peristaltic pump or sprung occlusion plate peristaltic pump, adjustment can be done by changing the force applied by the springs. Alternatively, in an unsprung peristaltic pump, the gap can be adjusted using a set screw to change the position of the occlusion plate or, alternatively, change parts can be used.

Furthermore, there is an advantage in using a pump with sprung rollers over a pump with a sprung occlusion plate. In a simple pump the number of rollers in contact with the tubing will be either 1 or 2 depending on the rotational position of the rollers. A pump with a sprung occlusion plate needs to apply sufficient force such that a sealing force is applied when 2 (or more) rollers are in contact with the tubing. That same sealing force is then double (or more) the force required when only one roller is in contact with the tubing. A pump with sprung rollers only applies the required force to each roller regardless of the rotational position of the rollers.

According to a further embodiment of the present invention, a silicone/PTFE composite tubing is arranged between the stepped occlusion plate and the at least one pump roller. In other words, the tubing may be made of a material mix comprising silicon and Polytetrafluoroethylene (PTFE). Specifically, PTFE is not mechanically reinforcing the silicon tubing by means of being a mesh or a web or alike. Rather, PTFE is reinforcing the silicon tubing by being part of the tubing material.

As silicone/PTFE composite tubing, any silicone/PTFE composite tubing can be used without limitation. Specifically, for example, STA-PURE PCS™ tubing manufactured by Watson Marlow Tubing, Fallmouth, UK, can be used. In comparison with standard silicone tubing, STA-PURE tubing only needs to be compressed to about 2.8 mm by the pump roller, i.e. 0.8 mm less compression compared to standard silicone tubing. In case of some pharmaceutical, chemical and solvent based processing applications, STA-PURE PFL™ reinforced fluoroelastomer tubing might be an alternative.

In general, the lower the modulus of elasticity of a tubing the greater the pressure fluctuation in a peristaltic pump. The silicone/PTFE composite tubing used according to the present invention has a high modulus of elasticity and hence is more resistant to hoop stresses, while still being easily pinched in a peristaltic pump. Therefore, there is less reverse flow of liquid to pressurise a section of the silicone/PTFE composite tubing and hence a smaller pressure fluctuation, which in turn leads to a lower protein damage in pumped protein solutions.

According to another aspect of the invention, there is provided a system for determining the relative robustness of different proteins in solution, the system comprising a reservoir for the solution, a peristaltic pump according to the above aspect or a particular embodiment thereof, a tubing loop of variable configuration and an in-line means of monitoring protein aggregation.

According to another aspect of the invention, there is provided a system for testing the effectiveness of different protein protective factors in a protein solution, the system comprising a reservoir for the solution, a peristaltic pump according to the above aspect or a particular embodiment thereof, a tubing loop of variable configuration and an in-line means on monitoring protein aggregation, the testing comprising: selecting one or more tubing and peristaltic pump configuration(s) known to create a level of protein damage, and then evaluating the effect of different protein protective factors on the protein damage.

Accordingly, there may be provided a system for testing the effectiveness of different protein protective factors in a protein solution, the system comprising a reservoir for the solution, a peristaltic pump as indicated above, a tubing loop of variable configuration and an in-line means of monitoring protein damage. As said system, a general bioprocessing tool can be used that can be fitted with a pump and tubing for the required purposes of determining protein damage. In general, off-line and in-line systems are possible. Furthermore, the system is not restricted to a cross-flow system. For example, a sample is loaded into the reservoir and the peristaltic pump drives the solution around the system. In this case, the peristaltic pump may be configured, for example, to a certain force or with tubing of different compositions, known to have varying effects on protein damage as detailed in the example part of the present application. In this system, protein damage could then be assessed by taking samples for off-line analysis or an in-line sensor, for example, an optical density sensor could be used to measure turbidity, measuring the level of insoluble protein aggregate.

The testing comprises the steps of: selecting one or more tubing and peristaltic pump configuration(s) known to create a level of protein damage, wherein the peristaltic pump is as described above, and then evaluating the effect of different protein protective factors, for example the pH, temperature, concentration, ionic strength, and/or excipients, on the protein damage.

According to a preferred embodiment of the present invention, the protective factors are a fluid that is pumped around the system and then removed to coat the internal surfaces of the one or more tubing prior to introducing the protein solution, or the protective factors are added to the protein solution.

According to another aspect of the present invention, there is further provided a method for evaluating the relative robustness of different proteins in solution, the method comprising the steps of: pumping a protein solution around a cross-flow filtration loop at various flow conditions prior to a filter being fitted to the cross-flow filtration loop, monitoring the rate of protein damage, then, after a given time, or a given pumped volume, or a given level of protein damage, introducing a filter to the loop, subsequently monitoring the level of protein damaged, and assessing whether the filter is removing protein aggregates, has no effect or contributes to protein damage.

According to another aspect of the present invention, there is further provided a method for evaluating the level of protein damage in protein solutions, the method comprising the steps of: pumping a protein solution around a cross-flow filtration loop at various flow conditions prior to a filter being fitted to the cross-flow filtration loop, monitoring the rate of protein damage, then, after a given time, or a given pumped volume, or a given level of protein damage, introducing a filter to the loop, subsequently monitoring the level of protein damaged, and assessing whether the filter is removing protein aggregates, has no effect or contributes to protein damage. This method could be carried out with a system similar to that as described above, wherein a filter could be introduced into the system loop at a given time point in the experiment in order to assess the impact of the filter on the processing of the protein and its effect on protein damage or promotion/removal of damaged protein.

The above-mentioned filter may be directly introduced or inserted into the loop, or may be fitted to the loop such that it can be added to the loop by actuating a suitable valve.

According to another aspect of the present invention, there is further provided a method of optimizing protein processing, including the steps of identifying a protein being able to be processed and optimizing small-scale processing of a processable protein by a peristaltic pump for cross-flow filtration, wherein the pump head includes a silicone/PTFE composite tubing.

According to a further embodiment of the present method, the optimization of the small-scale processing is terminated before the best result is achieved, in order to avoid an overcompensation of errors in a large-scale process, to which the small-scale process is to be transferred.

The meaning and advantages of the above method steps correspond to the steps described for the claimed use, such that a repetition of the same is omitted.

Said silicone/PTFE composite tubing can be used in a peristaltic pump for cross-flow filtration having a pump head.

According to another aspect of the invention there is provided a use of a silicone/PTFE composite tubing in the pump head of a peristaltic pump for cross-flow filtration in protein processing. In other words, the tubing is made of a material mix comprising silicon and Polytetrafluoroethylene (PTFE). Specifically, PTFE is not mechanically reinforcing the silicon tubing by means of being a mesh or a web or alike. Rather, PTFE is reinforcing the silicon tubing by being part of the tubing material.

As said silicone/PTFE composite tubing, any silicone/PTFE composite tubing can be used without limitation. Specifically, for example, STA-PURE PCS™ tubing manufactured by Watson Marlow Tubing, Fallmouth, UK, can be used. In comparison with standard silicone tubing, STA-PURE tubing only needs to be compressed to about 2.8 mm by the pump roller, i.e. 0.8 mm less compression compared to standard silicone tubing. In case of some pharmaceutical, chemical and solvent based processing applications, STA-PURE PFL™ reinforced fluoroelastomer tubing might be an alternative.

In general, the lower the modulus of elasticity of a tubing the greater the pressure fluctuation in a peristaltic pump. The silicone/PTFE composite tubing used according to the present invention has a high modulus of elasticity and hence is more resistant to hoop stresses, while still being easily pinched in a peristaltic pump. Therefore, there is less reverse flow of liquid to pressurise a section of the silicone/PTFE composite tubing and hence a smaller pressure fluctuation, which in turn leads to a lower protein damage in pumped protein solutions.

The remaining pulsation caused by the pump can be further reduced by a flow damper at the outlet of the pump. Flow dampers are well known for smoothing flow pulsations. By adopting the pump design as described herein in conjunction with silicone/PTFE composite tubing the pulsation is relatively small and the elasticity of a length of standard silicone tubing used between the pump and a downstream filter (for example) is sufficient to reduce pulsation to an acceptable low level (less than +/−10% pressure variation). If more damping is required then the length of elastic tubing can be increased or, alternatively, a more sophisticated flow damper can be used. A disadvantage of a flow damper is the variation in volume with pressure. As pressure increases the volume inside the flow damper (or tubing) increases and therefore there is error in the assumed volume recirculating around the cross-flow loop. In small-scale systems this problem is more acute than in large-scale systems. To remove the volume inaccuracy caused by pressure on the flow damper (or tubing), the volume/pressure relationship can be determined and then that information can be used to compensate for the recirculating volume during filtration.

According to a further embodiment, the protein processing includes identifying a protein being able to be processed and optimizing small-scale processing of a processable protein by the peristaltic pump including the tubing.

According to a further embodiment of the present use, the protein processing includes identifying a protein being able to be processed in larger scale.

The step of identifying a protein to be processed is carried out to test whether a protein is able to be processed by a peristaltic pump including the tubing at all, i.e. to test whether the protein is damaged by the processing, i.e. pumping, to such an extent that it cannot be reasonably used for further processing and reacting steps In case the test result is positive, the further step of optimizing small-scale processing of the processable protein by the peristaltic pump including the tubing is carried out in order to minimize the damage of the protein by the combination of tubing and peristaltic pump. After that the optimized protein processing conditions can be transferred to a large-scale processing for use in the industrial manufacture of proteins.

According to a further embodiment of the present use, the optimization of the small-scale processing is terminated before the best result is achieved, in order to avoid an overcompensation of errors in a large-scale process, to which the small-scale process is to be transferred.

This embodiment of the present invention avoids that the small-scale processing is "overoptimized", since in this case the processing is so specific for the small scale that again errors may occur in the large-scale process, i.e. the small-scale processing cannot be transferred to large-scale processing offhand.

According to an embodiment of the use the pump head comprises a stepped occlusion plate and at least one pump roller, wherein the tubing is arranged between the stepped occlusion plate and the at least one pump roller, wherein the stepped occlusion plate has an initial tubing compression lead in section,
a constant compression lead in section,
a lead in-to-pumping step,
a constant full tube compression pumping section,
a pumping-to-lead out step,
a constant compression lead out section, and
a final tubing decompression lead out section, wherein the initial tubing compression lead in section is adapted to provide an initial rapid tubing compression, wherein the constant compression lead in section and the constant compression lead out section are adapted to bring the internal tubing surfaces close to each other but not such that they are touching, wherein the lead in-to-pumping step and the pumping-to-lead out step are adapted to fully pinch the tubing closed by the at least one roller, and wherein the final tubing decompression lead out section is adapted to provide a rapid full decompression of the tubing.

According to an embodiment of the use the peristaltic pump is a sprung occlusion plate peristaltic pump, wherein the pressure of the sprung occlusion plate on the tubing can be adjusted.

According to an embodiment of the use the peristaltic pump is a sprung roller peristaltic pump, wherein the pressure of the at least one roller on the tubing can be adjusted.

According to an embodiment of the use a silicone/PTFE composite tubing is arranged between the stepped occlusion plate and the at least one pump roller.

Further features and advantages of the invention will become apparent from the following description and from the accompanying drawing, to which reference is made.

FIG. 1 shows a pump head according to an embodiment of the present invention.

In the following, an embodiment of the pump head (1) of the peristaltic pump as claimed in the present invention is described with reference to FIG. 1.

The pump head (1) as shown in FIG. 1 comprises a stepped occlusion plate (2) and four pump rollers (3). A tubing is to be arranged between the stepped occlusion plate (2) and the at least one pump roller (3). The stepped occlusion plate (2) has an initial tubing compression lead in section (4a), a constant compression lead in section (4b), a lead in-to-pumping step (4c), a constant full tube compression pumping section (4d), a pumping-to-lead out step (4e), a constant compression lead out section (4f), and a final tubing decompression lead out section (4g). The initial tubing compression lead in section (4a) is adapted to provide an initial rapid tubing compression. The constant compression lead in section (4b) and the constant compression lead out section (4f) are adapted to bring the internal tubing surfaces close to each other but not such that they are touching. The lead in-to-pumping step (4c) and the pumping-to-lead out step (4e) are adapted to fully pinch the tubing closed by the at least one roller (3). The final tubing decompression lead out section (4g) is adapted to provide a rapid full decompression of the tubing.

Summarizing, the present invention as claimed reduces the damage caused to proteins in a peristaltic pump and more generally is expected to reduce damage to sensitive fluids or suspensions. Furthermore, the present invention as claimed reduces the amount of pulsation from a peristaltic pump, wherein pulsation is often considered to be a disadvantage for many processes, reduces particular release, prolongs tubing life, provides a high pump rate stability, protects downstream system elements from excessive pressure, and allows the adjustment of small-scale-cross-flow filtration based systems to mimic larger scale systems in respect to protein damage they cause. Finally, the present invention as claimed provides a system to assess the relative robustness of proteins and the protective effect of carrier fluid composition in a directly relevant model.

The following specific example is provided for further illustrating the present invention and does not limit the scope of the present invention.

Example

Protein Aggregation Observation

A significant amount of protein aggregation was observed in a prototype system (Sartorius Stedim Biotech SA) when compared to a standard bench top cross-flow filtration system. Various components of the prototype system were decoupled to test for high shear zones. This test identified an aspect of the feed loop which was responsible for the significant protein aggregation effect.

DETAILED INVESTIGATION

Materials and Methods
Test Methodology
The common test method involved exposing 7 mL protein solution to a certain test condition for a period of time. Samples were then "borrowed" at regular time intervals for turbidity analysis (indicating insoluble protein aggregation) before returning to the test system. Unless otherwise stated, the common test method conditions were:
Pump speed: 7 mL/min
Transmembrane Pressure (TMP): 1500 mbar
Retentate pressure ($P_r$): 2000 mbar
Tubing: Pump head: Bioprene, Flow path: Silicone, 1.6 mm i.d.

Protein Solutions
Molecule 1: mAb
Molecule 2: mAb
Molecule 3: mAb-dAb
Protein Aggregation Measurement Samples were taken at regular time intervals for turbidity analysis using a spectrophotometer measuring at a wavelength of 600 nm.

Hardware Setup

Prototype (Sartorius Stedim Biotech SA)

Two different peristaltic pump designs were tested: a standard Watson Marlow pump (114DV OEM-pumphead), and a custom, in-house design pump according to the present invention. Backpressure or TMP was generated by an automated proportional valve.

Bench Scale System

A standard cross-flow filtration system configuration was used to evaluate relative performance of the Prototype system. A SciLog peristaltic pump was used in combination with a manually controlled pinch valve.

Results

Impeller

Confirmatory test that impeller is not the source of protein aggregation. Minimal change in the observed turbidity of the protein solution with time.

TABLE 1

10 mL molecule 2 protein solution exposed to 30% impeller power.

| Time | Molecule 2 OD$_{600}$ |
| --- | --- |
| 20 mins | 0.016 |
| 20 mins | 0.043 |

Benchmark Testing

Standard configurations were tested in both cross-flow filtration scale systems to benchmark performance (Table 2). Prototype system scale benchmark test reveals a higher rate of protein aggregation when compared to the standard bench scale configuration. At both scales, application of back pressure alleviates the protein aggregation effect. Halving the cross-flow rate also appears to halve the rate at which protein aggregates (Table 3). These factors indicate a direct correlation between mechanical action of the peristaltic pump and the protein aggregation event.

TABLE 2

Molecule 2 protein solution exposed to the different cross-flow filtration scale systems. Volumes and cross-flow rates are scaled linearly in order to maintain pump action:protein molecule ratio.

| | Molecule 2 System | | | |
| --- | --- | --- | --- | --- |
| | Prototype system 7 mL protein 7 mL/min cross-flow rate Bioprene in the pump head | | Benchscale 35 mL protein 35 mL/min cross-flow rate Norprene in the pump head | |
| Test Condition | No backpressure | 2 bar backpressure | No backpressure | 2 bar backpressure |
| 15 mins | 0.244 | 0.198 | 0.053 | 0.052 |
| 30 mins | 0.444 | 0.411 | 0.109 | 0.094 |
| 45 mins | 0.646 | 0.596 | 0.161 | 0.136 |
| 60 mins | 0.832 | 0.793 | 0.211 | 0.174 |

TABLE 3

Molecule 2 protein solution exposed to different cross-flow rates in the prototype system.

| | Molecule 2 7 mL protein Bioprene in the pump head No backpressure | |
| --- | --- | --- |
| Test Condition | 7 mL/min cross-flow rate | 3.5 mL/min cross-flowrate |
| 15 mins | 0.244 | — |
| 30 mins | 0.444 | — |
| 45 mins | 0.646 | 0.351 |
| 60 mins | 0.832 | 0.461 |
| 90 mins | — | 0.652 |

Effect of Pump Design

An in-house, custom designed peristaltic pump according to the present invention was investigated to determine if the protein aggregation effect could be influenced by redesign of the pump. Table 4 shows that the redesigned pump effectively reduces the rate of protein aggregation. Decreasing the force applied at each roller pass is also shown to reduce protein aggregation (Table 5).

TABLE 4

Molecule 2 protein solution exposed to two different peristaltic pump designs.

| | Molecule 2 | |
| --- | --- | --- |
| Test Condition | Watson Marlow pump | In-house designed, custom pump |
| 15 mins | 0.244 | 0.152 |
| 30 mins | 0.444 | 0.327 |
| 45 mins | 0.646 | 0.493 |
| 60 mins | 0.832 | 0.652 |

TABLE 5

Effect of pressure investigated by reducing the force applied by the back plate onto the peristaltic pump.

| | Molecule 2 In- house designed, custom pump | |
| --- | --- | --- |
| Test Condition | Pump roller force 5 bar | Pump roller force 2.5 bar |
| 15 mins | 0.042 | 0.05 |
| 30 mins | 0.087 | 0.078 |
| 45 mins | 0.134 | 0.107 |
| 60 mins | 0.174 | 0.135 |

Effect of Tubing Material

Different tubing materials were tested to determine their effect on protein aggregation (Table 6). In the first instance, a buffer solution (no protein) was tested to rule out the fact that the turbidity measurements were as a result of particle release from the tubing. Comparing 6 (iv) with 6 (ii), there is a clear positive effect on the rate of protein aggregation with tubing material in the flow path. Silicone tubing in the pump head drastically reduces the increase in turbidity with time for the protein sample. Similar levels of protein aggregation occur when comparing either 6 (v) with 6 (iv) or 6 (ii) with 6 (iii), illustrating that the protein aggregation effect is as a direct result of the bioprene tubing in the pump head itself, rather than any exposure to this material when not in a high mechanical force environment.

TABLE 6

Effect of different tubing materials on the protein aggregation.

| | Molecule | | | |
|---|---|---|---|---|
| N/A | 2 | | | |

In- house designed, custom pump
No back pressure

| Test Condition | i<br>Buffer only | ii<br>Standard setup<br>Pump head: Bioprene<br>Flow path: Silicone | iii<br>Pump head: Bioprene<br>Flow path: Bioprene | iv<br>Pump head: Silicone<br>Flow path: Silicone | v<br>Pump head: Silicone<br>Flow path: Bioprene |
|---|---|---|---|---|---|
| 15 mins | 0.001 | 0.152 | 0.157 | 0.048 | 0.04 |
| 30 mins | 0.006 | 0.327 | 0.3 | 0.095 | 0.081 |
| 45 mins | 0.012 | 0.493 | — | 0.145 | 0.122 |
| 60 mins | 0.02 | 0.652 | — | 0.175 | — |

Confirmation in Multiple Molecules

This protein aggregation effect was subsequently confirmed in two different molecules (Table 7). Results here confirm that the combination of an in-house designed peristaltic pump according to the present invention with a silicone based tubing drastically reduce the protein aggregation effect.

TABLE 7

Two different molecules were tested to ensure that protein aggregation effects that had been demonstrated were not molecule specific.

| | Molecule | | | |
|---|---|---|---|---|
| | 1 | | 3 | |
| Test Condition | Watson Marlow<br>Pump head: Bioprene | In-house designed, custom pump<br>Pump head: Silicone | Watson Marlow<br>Pump head: Bioprene | In-house designed, custom pump<br>Pump head: Silicone |
| 15 mins | 0.112 | 0.02 | 0.16 | 0.077 |
| 30 mins | 0.286 | 0.06 | 0.348 | 0.121 |
| 45 mins | 0.474 | 0.030 | 0.545 | 0.163 |
| 60 mins | 0.645 | 0.042 | 0.717 | 0.207 |

Product Solution

Silicone tubing has a short mechanical life so is therefore unsuitable for extended periods of time in a peristaltic pump. STA-Pure (platinum-cured silicone rubber, reinforced with expanded polytetrafluoroethylene (ePTFE)) was investigated as a suitable replacement (Table 8). For both molecules investigated, it appears that the positive effect that the silicone tubing chemical composition has on protein aggregation is amplified by the mechanical effect of the reinforced tube structure.

TABLE 8

Effect of two different silicone tubes with different mechanical properties investigated with two different molecules.

| | Molecule | | | |
|---|---|---|---|---|
| | 2 | | 3 | |
| | In- house designed, custom pump | | | |
| Test Condition | Pump head:<br>TuFlux | Pump head:<br>STA-Pure | Pump head:<br>TuFlux | Pump head:<br>STA-Pure |
| 15 mins | 0.055 | 0.015 | 0.103 | 0.063 |
| 30 mins | 0.089 | 0.021 | 0.149 | 0.064 |
| 45 mins | 0.122 | 0.026 | 0.194 | 0.069 |
| 60 mins | 0.156 | 0.03 | 0.239 | 0.076 |

The invention claimed is:

1. A method for evaluating the relative robustness of different proteins in solution, the method comprising the steps of:
    pumping a protein solution around a cross-flow filtration loop at various flow conditions prior to a filter being fitted to the cross-flow filtration loop,
    monitoring the rate of protein damage,
    then, after a given time, or a given pumped volume, or a given level of protein damage, introducing a filter to the loop,
    subsequently monitoring the level of protein damaged, and
    assessing whether the filter is removing protein aggregates, has no effect or contributes to protein damage,
    wherein pumping the protein solution is carried out with a peristaltic pump suitable for cross-flow filtration in protein treatment having a pump head, wherein the pump head comprises a stepped occlusion plate and at least one pump roller, wherein a tubing is to be arranged between the stepped occlusion plate and the at least one pump roller,
    wherein the stepped occlusion plate comprises:
        an initial tubing compression lead in section,
        a constant compression lead in section,
        a lead in-to-pumping step,
        a constant full tube compression pumping section,
        a pumping-to-lead out step,
        a constant compression lead out section, and
        a final tubing decompression lead out section,
    wherein the initial tubing compression lead in section is adapted to provide an initial rapid tubing compression, wherein the constant compression lead in section and the constant compression lead out section are adapted to bring the internal tubing surfaces close to each other but not such that they are touching, wherein the lead in-to-pumping step and the pumping-to-lead out step are adapted to fully pinch the tubing closed by the at least one roller, and wherein the final tubing decompression is adapted to provide a rapid full decompression of the tubing.

2. The method according to claim 1, wherein the peristaltic pump is a sprung occlusion plate peristaltic pump, wherein the pressure of the sprung occlusion plate on the tubing can be adjusted.

3. The method according to claim 1, wherein the peristaltic pump is a sprung roller peristaltic pump, wherein the pressure of the at least one roller on the tubing can be adjusted.

4. The method according to claim 1, wherein a silicon/PTFE composite tubing is arranged between the stepped occlusion plate and the at least one pump roller.

5. A system for determining the relative robustness of different proteins in a solution, the system comprising a reservoir for the solution, the peristaltic pump, a tubing loop of variable configuration and an in-line means of monitoring protein aggregation, wherein the peristaltic pump is a peristaltic pump suitable for cross-flow filtration in protein treatment having a pump head, wherein the pump head comprises a stepped occlusion plate and at least one pump roller, wherein a tubing is to be arranged between the stepped occlusion plate and the at least one pump roller, wherein the stepped occlusion plate comprises:

an initial tubing compression lead in section,
a constant compression lead in section,
a lead in-to-pumping step,
a constant full tube compression pumping section,
a pumping-to-lead out step,
a constant compression lead out section, and
a final tubing decompression lead out section, wherein the initial tubing compression lead in section is adapted to provide an initial rapid tubing compression, wherein the constant compression lead in section and the constant compression lead out section are adapted to bring the internal tubing surfaces close to each other but not such that they are touching, wherein the lead in-to-pumping step and the pumping-to-lead out step are adapted to fully pinch the tubing closed by the at least one roller, and wherein the final tubing decompression lead out section is adapted to provide a rapid full decompression of the tubing.

6. The system according to claim 5, wherein the peristaltic pump is a sprung occlusion plate peristaltic pump, wherein the pressure of the sprung occlusion plate on the tubing can be adjusted.

7. The system according to claim 5, wherein the peristaltic pump is a sprung roller peristaltic pump, wherein the pressure of the at least one roller on the tubing can be adjusted.

8. The system according to claim 5, wherein a silicone/PTFE composite tubing is arranged between the stepped occlusion plate and the at least one pump roller.

9. The system according to claim 5, wherein a filter is fitted to the tubing loop.

* * * * *